United States Patent [19]

Bullard et al.

[11] Patent Number: 5,102,324

[45] Date of Patent: Apr. 7, 1992

[54] PRECISION TIPPING DEVICE FOR SURGICAL CATHETERS

[75] Inventors: Gary C. Bullard, Troi; William J. Gahara, Nashua, both of N.H.

[73] Assignee: Worldwide Medical Plastics Inc., Nashua, N.H.

[21] Appl. No.: 467,896

[22] Filed: Jan. 22, 1990

[51] Int. Cl.$^5$ .............................................. B29C 31/08
[52] U.S. Cl. .................................. 425/135; 264/40.6; 264/40.7; 425/150
[58] Field of Search ...................... 425/150, 126.1, 135, 425/384, 807; 264/40.5, 40.7, 40.6; 409/64, 69, 72, 75, 80, 133, 143, 153; 269/244

[56] References Cited

U.S. PATENT DOCUMENTS

| | | | |
|---|---|---|---|
| 4,264,294 | 4/1981 | Ruiz | 425/467 |
| 4,404,159 | 9/1983 | McFarlane | 425/393 |
| 4,561,814 | 12/1985 | Dahlgren, Jr. et al. | 409/80 |
| 4,592,712 | 6/1986 | Gutjahr | 425/145 |
| 4,592,714 | 6/1986 | Gutjahr | 264/40.5 |
| 4,661,300 | 4/1987 | Daugherty | 264/40.6 |
| 4,861,529 | 8/1989 | Groebli et al. | 425/155 |

OTHER PUBLICATIONS

Mechanical Design and Systems Handbook, 2nd Ed; Harold Rothbart, Editor in Chief; McGraw-Hill Book Company; New York, NY; 1985; pp. 41.33–41.38.

Primary Examiner—Jay H. Woo
Assistant Examiner—W. J. Matney, Jr.
Attorney, Agent, or Firm—St. Onge Steward Johnston & Reens

[57] ABSTRACT

A device is provided for precision tipping catheters with repeatable accuracy. The device includes a die, a thermal heater for the die, a clamping pad for holding an untipped catheter in an aligned position, a lead screw for moving the catheter into and out of the die a precise distance, and a forced air cooler for cooling the tipped catheter. Preferably, the lead screw is rotated by a stepping motor.

18 Claims, 5 Drawing Sheets

PRECISION TIPPING DEVICE FOR SURGICAL CATHETERS

TECHNICAL FIELD

This invention relates to catheter tipping devices and methods and, more specifically, to devices and methods for precision tipping of surgical catheters.

BACKGROUND ART

Tipping devices and methods for catheters are well known in the art. Such devices and methods employ a variety of features in order to meet a variety of different catheter tipping needs. For example, U.S. Pat. No. 4,661,300 discloses a method and apparatus for flashless tipping of an I.V. catheter. I.V. catheters are frequently used to nourish patients by injecting glucose, saline and like solutions directly into their veins. I.V. catheters are not high precision catheters. In this regard, methods and devices for tipping I.V. catheters are chiefly directed to efficiency, simplicity of production method, and high production output.

For other applications such as arterial catheters or other surgical catheters, precision manufacture and repeatable accuracy of manufacture are the primary goals.

Precision manufacture, however, is difficult or impossible with prior art methods and devices which comprise air and other fluid cylinders, and a.c. motors and belts to advance the catheter into a die. Tipping dies are typically heated with RF heaters. Further, repeatable accuracy of manufacture resulting in nearly identical catheters is similarly difficult or impossible with prior art methods and devices. There exists, therefore, a present need for devices and methods for the high precision and repeatably accurate tipping of catheters, especially arterial and other surgical catheters.

SUMMARY OF THE INVENTION

Accordingly, it is an object of this invention to provide a method and device for precision tipping of catheters. It is another object of this invention to provide a method and device for tipping catheters with repeatable accuracy. It is a further object of this invention to provide a device for tipping catheters comprising a stepping motor for advancing the catheter into a tipping mold. It is still another object of this invention to provide a device for tipping catheters comprising a thermally heated die.

This invention relates to devices for precision tipping catheters with repeatable accuracy. The device comprises a die, means for heating and preferably thermally heating the die, a clamping pad for holding an untipped catheter in an aligned position, means for moving the catheter into the die a precise distance, and means for cooling and removing the tipped catheter. Preferably, the moving means comprises a stepping motor. Additionally, the motor preferably twists a screw to which the clamping pad is mounted for precision axial movement toward the die.

In another aspect, this invention relates to a method for tipping catheters with the above device. The method comprises providing a die, heating the die to a molding temperature, inserting a hypo into the catheter to mold its inside diameter, aligning the catheter with the die, advancing the catheter into the die to within one one-hundredth of an inch precision, retaining the catheter within the die for a dwell time, cooling the catheter by forcing air through the hypo, removing the catheter including flashing from the die, and trimming the flashing from the tip.

The invention and its particular features will become more apparent from the following detailed description when considered with reference to the accompanying drawings.

DETAILED DESCRIPTION

Figure 1:
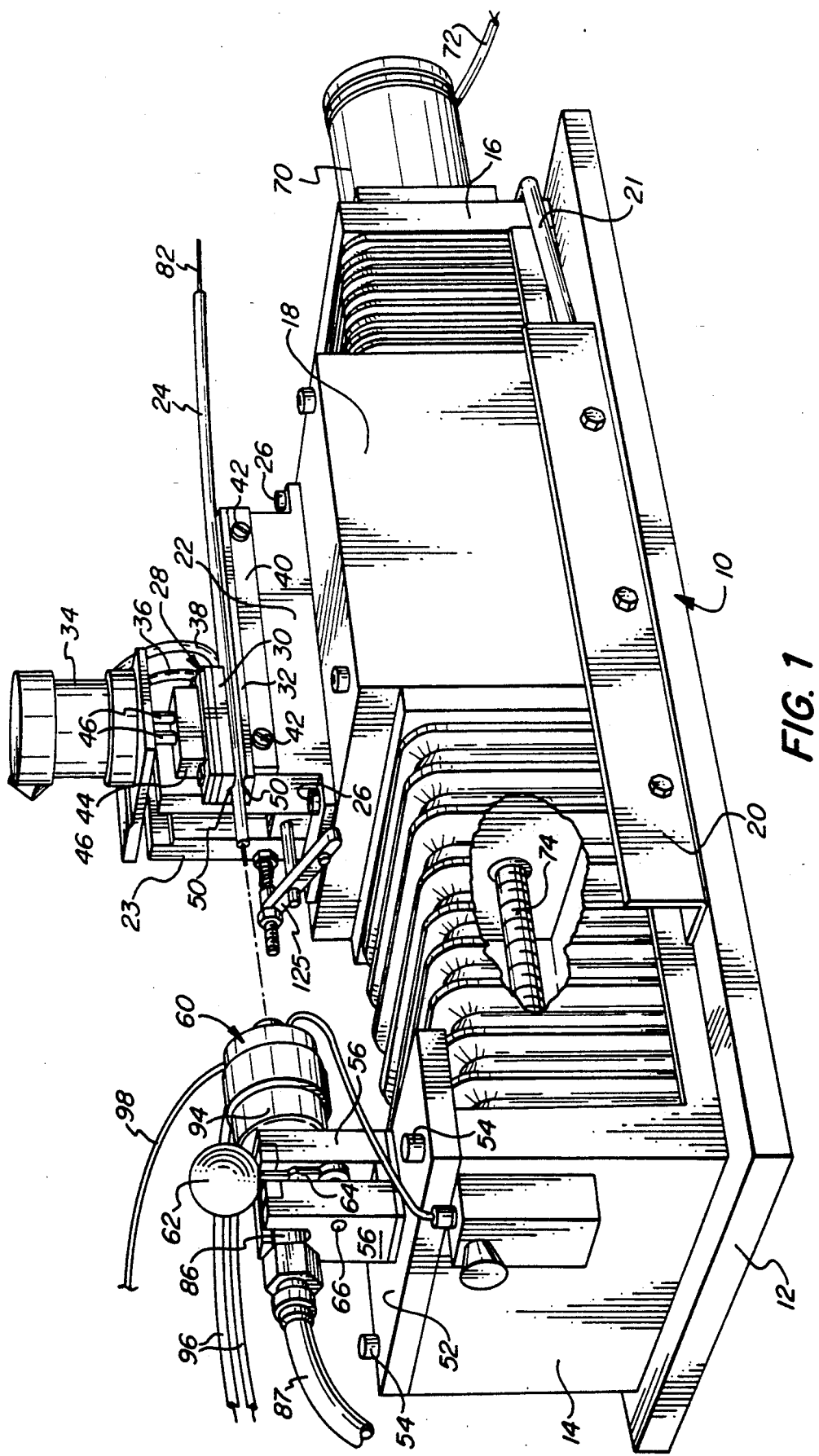
FIG. 1 is a front perspective view of a catheter tipping device in accordance with the invention.

A front perspective view of a precision tipping device for surgical catheters 10 ("catheter tipper") is shown in FIG. 1. Catheter tipper 10 generally comprises a base 12, end or side walls 14 and 16, and a carriage 18 slidably mounted on base 10 between side walls 14 and 16. Housing 20 encloses over-travel limit switches (not shown) which prevent, via line 21, carriage 18 from moving too far forward.

Carriage 18 includes a bracket 22 for mounting a catheter 24 to be tipped. Mounting bracket 22 is attached to carriage 18 by screws 26 or the like. A clamping pad assembly 28 holds catheter 24 in place. Clamping pad assembly 28 comprises an upper pad 30, a lower pad 32, and an air cylinder 34 or other clamping means. Air cylinder 34 is mounted to upright 23, and is actuated and deactuated through fluid lines 36 and 38.

Lower pad 32 is fixed directly to mounting bracket 22 with a retaining strip 40 secured by screws or the like 42. Upper pad 30 is fixed however to platform 44 which may be advanced toward lower pad 32 by rods 46 of air cylinder 34. Both upper and lower pads 30 and 32 include grooves 50 therein so that catheter 24 is firmly held without pinching or otherwise deforming its cross sectional shape. Further, pads 30 and 32 are preferably formed from rubber and are easily replaceable in order that their grooves properly match the outside diameter of catheter 24.

Side wall 14 also includes a bracket 52 mounted thereto with screws 54 or the like. Bracket 52 includes upstanding portions 56 for mounting a tipping mold 60. Upstanding portions 56 are positioned on bracket 52 in conjunction with clamping pad assembly 28 on bracket 22 to bring tipping mold 60 into axial alignment with catheter 24.

Tipping mold 60 is relatively quickly secured with clamping ball 62 which screws down on shaft 64 to hold tipping mold 60 within upstanding portions 56. Shaft 64 pivots about point 66 to enable relatively quick and easy replacement of tipping mold 60 to provide a variety of possible catheter tips.

A stepping motor 70 is mounted to side wall 16. Stepping motor 70 is actuable via line 72 to twist or rotate screw 74. Screw 74 is rotatably mounted (not shown) in side wall 14 and is axially aligned parallel to the path of catheter 24 into tipping mold 60.

Prior art tipping machines typically utilize air rams or a.c. motors and belts to advance catheters into molds. The devices provide neither precision catheter tips nor tips having repeatable accuracy. The dominant limitation is control of the distance the catheter is advanced into the die. Other limitations include monitoring and control of die temperature, dwell time within the die, air cooling time/temperature, and the like.

Stepping motor 70 used in catheter tipper 10 advances catheter 24 into tipping mold 60 to within one one-hundredth of an inch, and preferably to within one-half of one one-thousandth of an inch axial precision providing precision catheter tips. Further, stepping motor 70 also removes or retracts catheter 24 out of tipping mold 60 to within one one-hundredth of an inch, and preferably to within one-half of one one-thousandth of an inch axial precision permitting precision catheter tipping with repeatable accuracy.

Stepping motor 70 functions to twist screw 74 to within very small fractions of a rotation; thereby, axially displacing carriage 18—mounted to screw 74—by even smaller dimensions. In this regard, stepping motor 70 is controllable to within about one four-hundredth of a rotation. Further, screw 74 is preferably provided with about five threads per inch so that one rotation of the screw advances catheter 24 about one-fifth of an inch. Limiting switches within housing 20 stop stepping motor 70 along line 21 from advancing carriage 18 too close to tipping mold 60.

Figure 2:
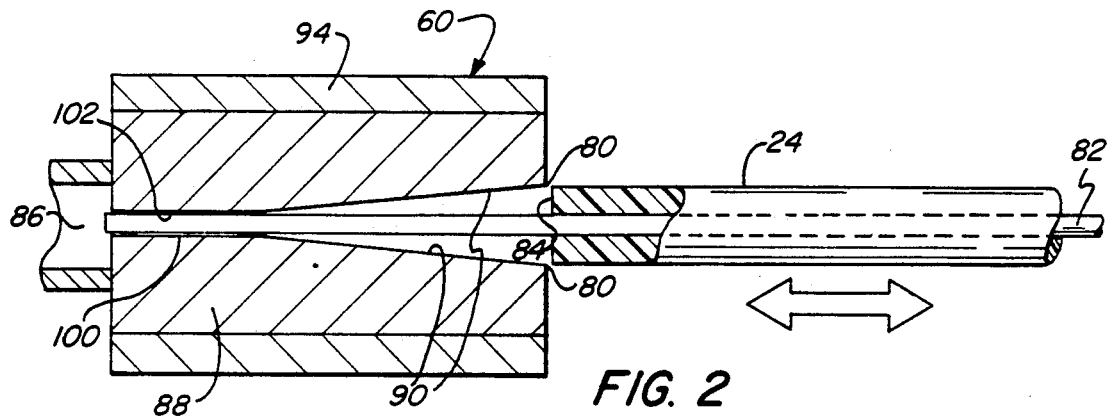
FIG. 2-5 are partial front cross-sectional views of the catheter tipping device of FIG. 1 showing various stages of the tipping process.

Referring now to FIGS. 2 to 5, the formation of a catheter tip is shown in stepwise schematic fashion. In FIG. 2, catheter 24 is shown at the cavity or opening 80 of tipping mold 60. Opening 80 preferably has a diameter slightly greater than the outside diameter of catheter 24. At this point the catheter has been advanced a "long stroke" from an initial or mounting position to cavity 80.

Figure 3:
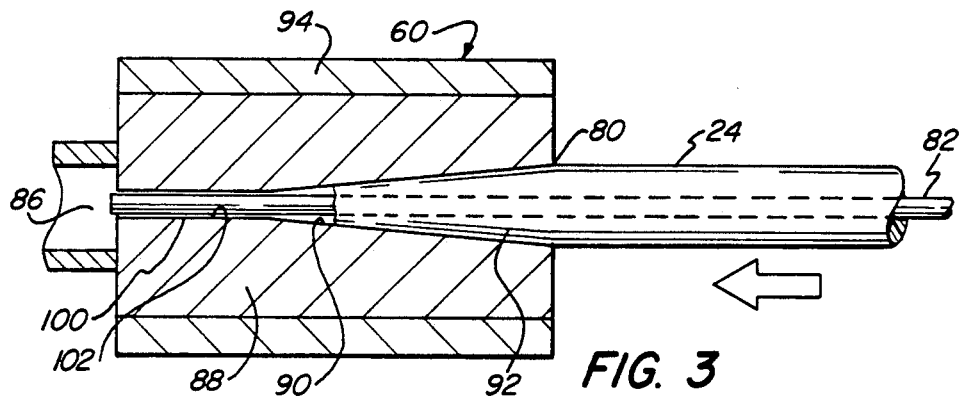
Figure 4:
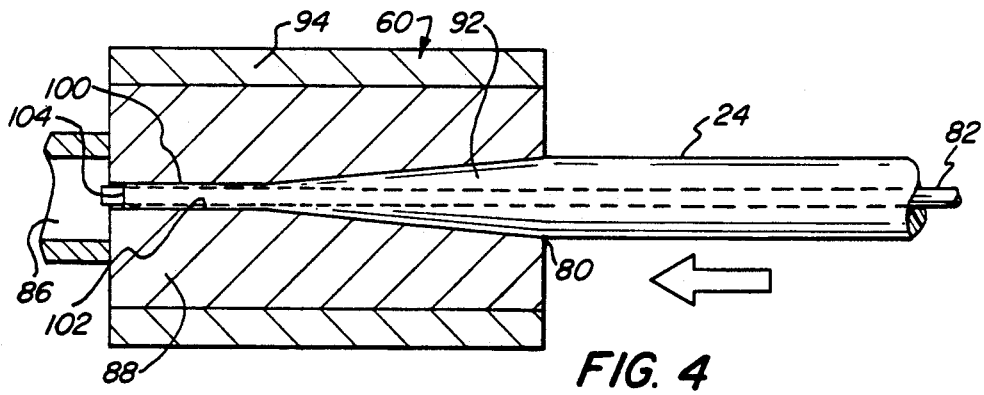

Catheter 24 is partially cut away to reveal a hypo 82 inserted therein. Hypo 82 preserves the inside diameter of catheter 24 during tipping. In this regard, hypo 82 preferably extends beyond untipped end 84 of catheter 24 in order to form an inside diameter throughout the entire tip. Referring now to FIG. 4, hypo 82 is also preferably hollow and, after molding of the tip, is in communication with air cooling sleeve 86 which abuts die 88 in tipping mold 60. In this regard, cooling air passes through hypo 82 to cool catheter 24 from the inside. As shown in FIG. 1, cooling sleeve 86 is connectable to an air line 87. Referring now to FIG. 3, converging inner walls 90 of die 88 mold or form a tip 92 on catheter 24 as it is advanced into tipping mold 60. In this regard, die 88 has been preheated preferably by a thermal element 94—to a desired temperature of between about 300° F. to about 450° F. Most prior art tipping devices have RF heaters, however, thermal heaters are preferred because they provide more complete and thorough heating. As shown in FIG. 1, thermal element 94 is actuated via lines 96 and controlled via line 98 leading to a thermocouple or the like (not shown) embedded in die 88.

Referring now to FIG. 4, catheter 24 has at this point been completely advanced a "short stroke" from the beginning of cavity 80 into tipping die 60 to form tip 92. Converging walls 90 of heated die 88 terminate in a sleeve or axial outlet 100 having substantially parallel walls 102. The diameter of the sleeve formed by walls 102 is preferably slightly greater than the inside diameter of catheter 24 or slightly greater than the outside diameter of hypo 82. Once tip 92 is formed, excess catheter material or flashing 104 oozes or flows along sleeve 100. After the molded catheter 24 is cooled, it is removed from tipping die 60 with flashing 104 attached.

Figure 5:
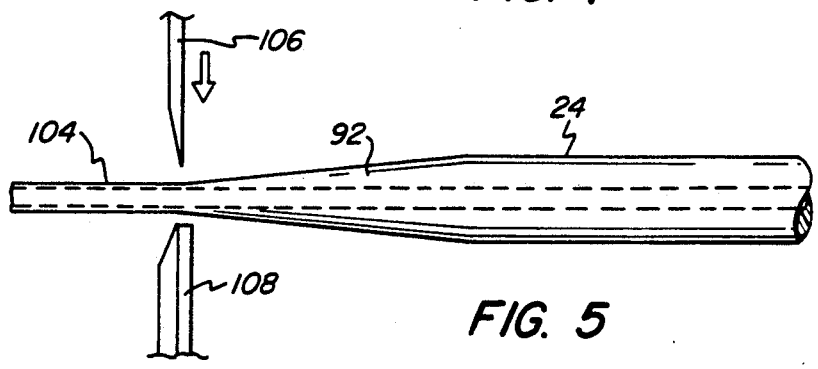

Referring now to FIG. 5, flashing 104 is removed from tip 92 with a cutting blade 106 and anvil 108 or like means.

Figure 6:
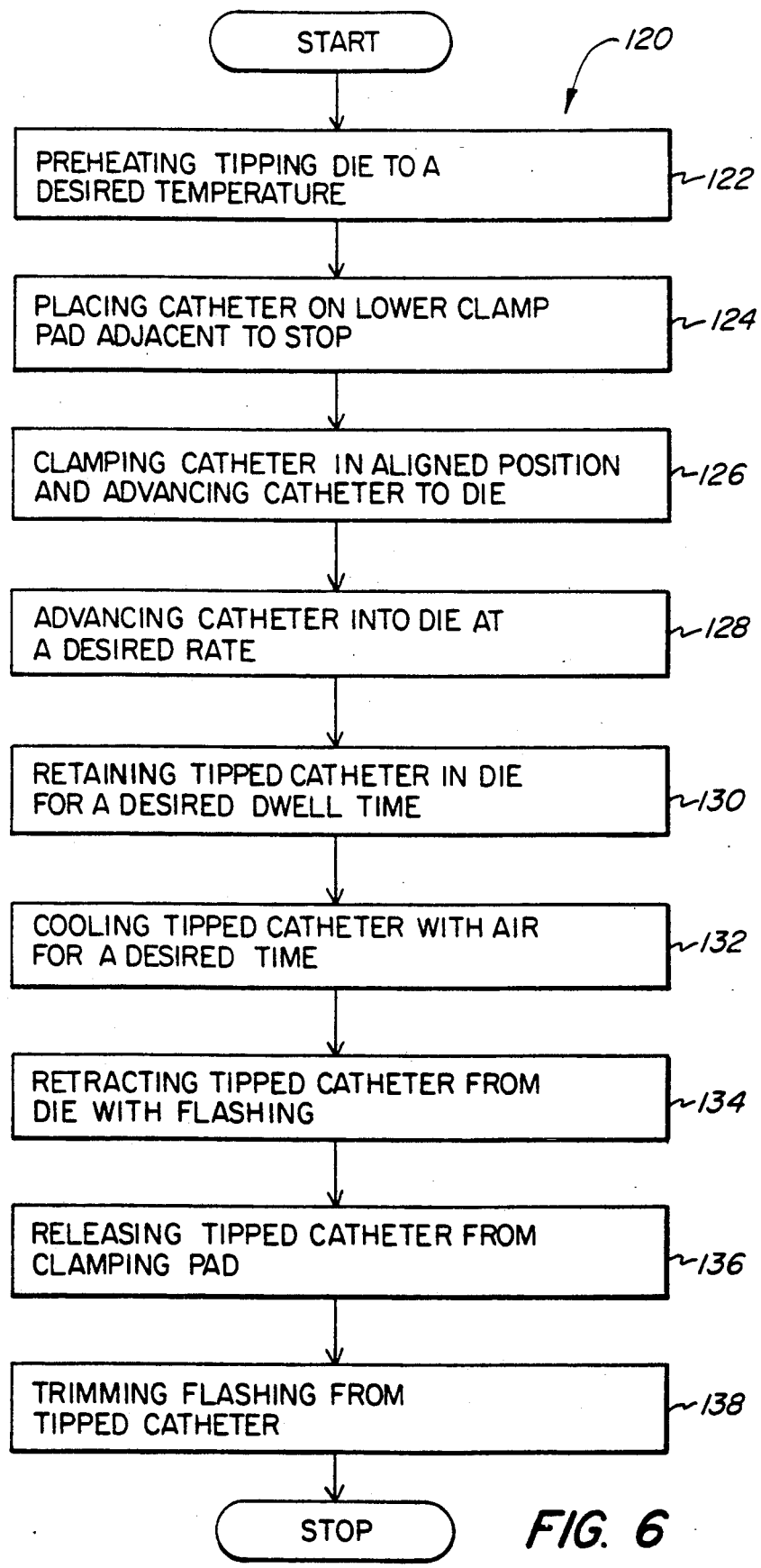
FIG. 6 is a flow diagram illustrating a method of tipping a catheter in accordance with the invention.

Referring now to FIG. 6, a method 120 of tipping a catheter in accordance with the invention is generally shown. Tipping mold 60 which comprises die 88 and thermal element 94 is preheated at 122 to a desired temperature. An untipped catheter 24 is placed at 124 on lower clamp pad 32. Returning briefly to FIG. 1, catheter 24 is held by clamping pad assembly 28 at an initial or zero position set by adjustable stop 125. In order to provide repeatable accuracy, each catheter 24 must be properly set in the initial position adjacent stop 125. Returning to FIG. 6, method 120 continues at 126 where catheter 24 is clamped and held in an aligned position with tipping die 60, and where it is advanced a "long stroke" from the initial position to cavity 80 of tipping die 60. Catheter 24 is then advanced at 128 a "short stroke" from cavity 80 into heated die 88 through cavity 80 for a desired distance at a desired rate to mold a catheter tip 92. At 130, catheter 24 with tip 92 remain in heated die 88 for a desired dwell time. Next catheter 24 and tip 92 are cooled at 132 with air for a desired time or to a desired temperature. Once cooled, tipped catheter 24 is removed from tipping die 60 with flashing 104 attached thereto. Tipped catheter 24 is released at 136 from clamping pad assembly 28, and flashing 104 is trimmed at 138 from catheter 24 to complete method 120.

Figure 7:
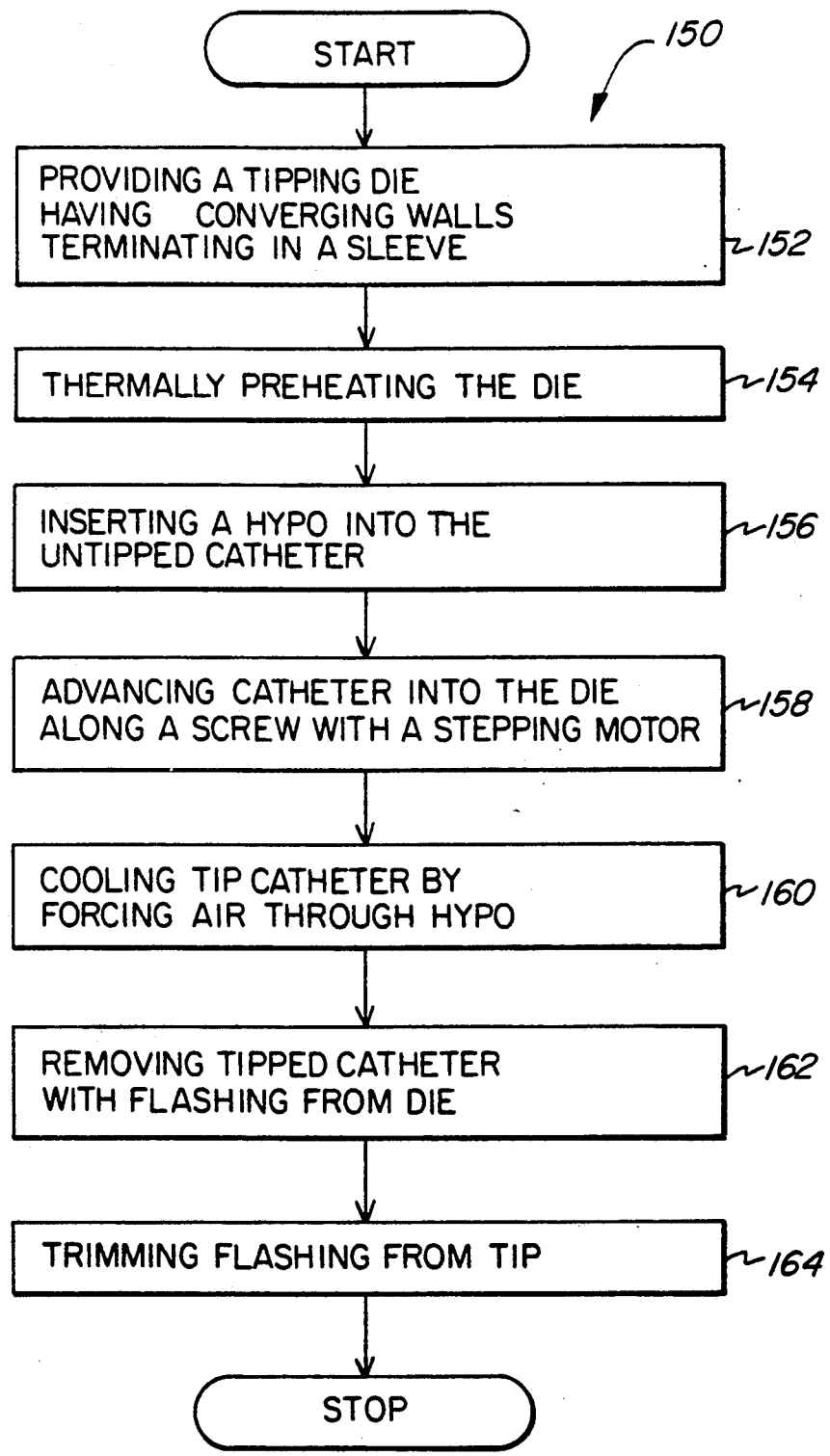
FIG. 7 is a flow diagram illustrating a method of tipping a catheter with the device of FIG. 1.

Referring now to FIG. 7, a method 150 of tipping a catheter with device 10 of FIG. 1 is illustrated. Tipping mold 60 having converging walls 90 terminating in a sleeve 100 having substantially parallel walls is provided at 152. Tipping mold 60 is thermally preheated at 154 and regulated at a desired temperature. Next, hypo 82 is inserted at 156 in untipped catheter 24 so that it extends beyond the end 84 thereof to be tipped. Catheter 24 is advanced at 158 along screw 74 with stepping motor 70 into tipping die 60 with relatively high precision. Next, catheter 24 with tip 92 is cooled at 160 by forcing air through hypo 82. Tipped catheter 24 is then removed at 162 from tipping mold 60 with flashing 104 attached to tip 92 thereof. Lastly, flashing 104 is trimmed at 164 from tip 92 with blade 106 and anvil 108, or like means.

Figure 8:
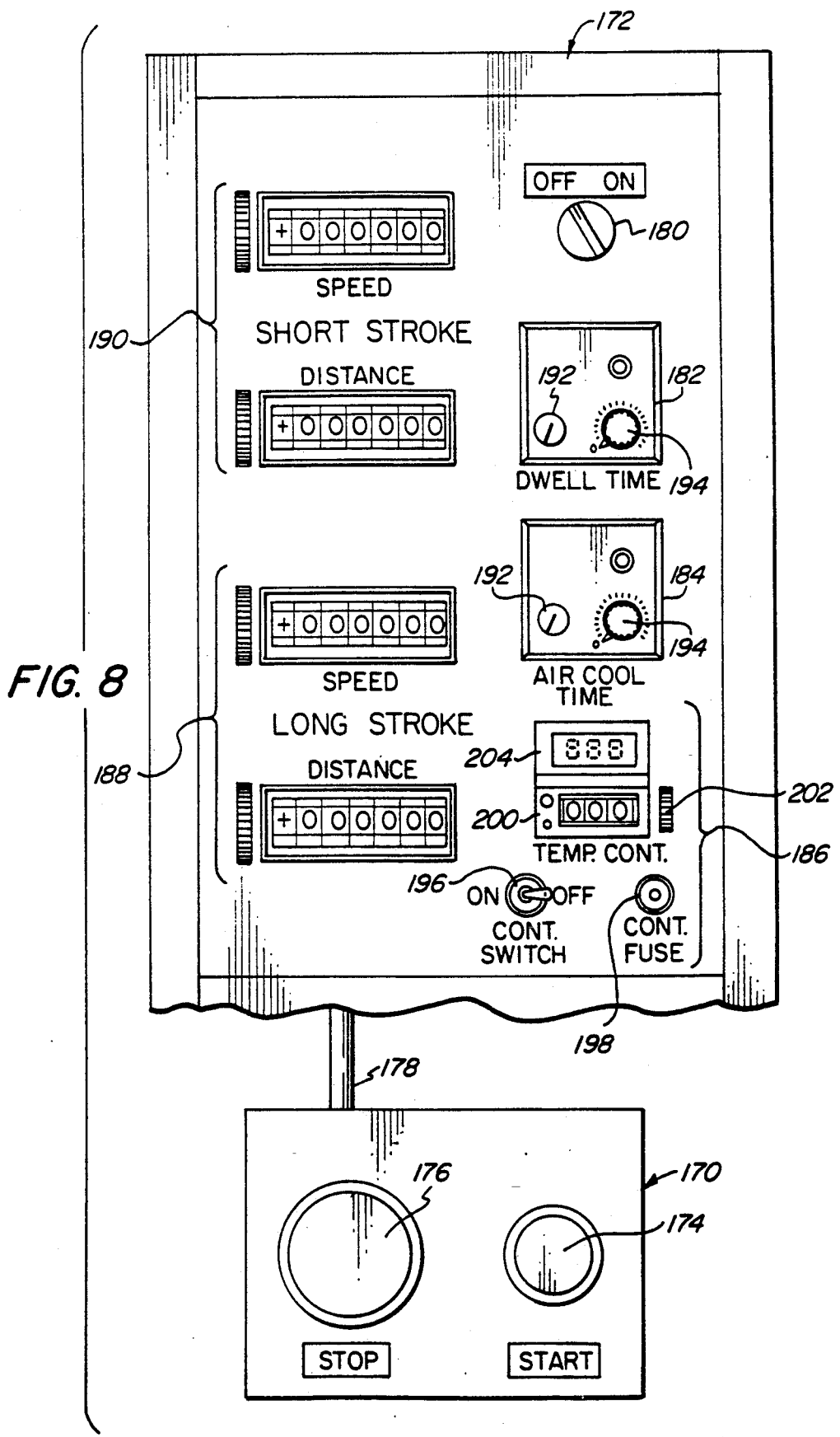
FIG. 8 is a front view of controllers used to operate the device of FIG. 1.

Referring now to FIG. 8, a front view of controllers 170 and 172 for operating device 10 of FIG. 1 are shown. Controller 170 comprises a start button 174 and a stop button 176 which enable and disenable the functions of controller 172 along line 178. Controller 170 is preferably located near device 70 as stop button 176 enhances safety.

Controller 172 provides all the functions essential to precision tip catheter 24. Specifically, controller 172 includes an ON-OFF switch 180, a dwell timer 182, an air cool timer 184, a temperature controller 186, a "long stroke" controller 188, and a "short stroke" controller 190.

Dwell and air cool timers 182 and 184 are adjustable by potentiometers 192 or the like and provide a read via analog meters 194. Dwell timer 182 causes—along line 72 (see FIG. 1)—stepping motor 70 to pause with catheter 24 within tipping mold 60. Air cool timer 184 actuates a compressor (not shown) which provides air along line 87 to cooling sleeve 86 and hypo 82 (see FIGS. 1-4).

Temperature controller 186 includes a separate power switch 196, a fuse 198, a readout 200 indicated desired temperature as selected by thumbwheel 202 or like means and an actual temperature LED readout 204 which receives input from thermocouple line 98 (see FIG. 1). The desired temperature is provided along lines 96 leading to thermal elements 94 in die 88 (see FIGS. 1-4).

Long and short stroke controllers 188 and 190 each include readouts 206 indicating the desired distance of the "strokes" as selected by thumbwheels 208 or like means, and include readouts 210 indicating the desired speed of the "strokes" as selected by thumbwheels 212 or like means. The long and short strokes are effected by stepping motor 70 along line 72 (see FIG. 1). Additionally, prior to effecting the long stroke—bringing catheter 24 to tipping die 60—upon starting the tipping process with button 174, catheter 24 must be held or clamped in the initial position by clamping pad assembly 28 activated by air cylinder 34 along lines 36 and 38 (see FIG. 1).

The functions of controller 172 may be relatively easily set by hand and thus may be relatively easily changed as required by different tipping dies, different catheter material or size, or different tips.

Although the invention has been described with reference to particular embodiments, features, materials of construction and the like, these are not intended to exhaust all possible features, and indeed many other modifications and variations will be ascertainable to those of skill in the art.

What is claimed is:

1. A device for precision tipping surgical catheters comprising:
   a die for molding a tip on a catheter;
   means for heating said die;
   means for holding an untipped catheter in an aligned position relative to said die;
   means for axially moving the held catheter into said die comprising:
   a screw,
   a step motor for rotating said screw, and
   a carriage axially adjustably mounted to said screw, said carriage for mounting said holding means to said screw such that rotating said screw moves the catheter into said die to provide a precision tip to the catheter; and
   a cool timer;
   means for enabling adjustment of said cool timer to select a desired cool time without reprogramming said cool timer; and
   means responsive to said cool timer for providing a flow of air through the tipped catheter during the desired cool time, said air providing means connected to said die.

2. The device of claim 1 comprising a hypo inserted into the catheter so that an end of said hypo extends beyond an end of the catheter, and wherein said air providing means is adapted to provide a flow of air through said hypo to cool the tipped catheter.

3. The device of claim 2 wherein said axial moving means further comprises means for enabling selection of a desired axial advancing rate without reprogramming said axial moving means, and wherein said step motor is responsive to said axial advancing rate selection enabling means for axially advancing the catheter into said die at the desired rate.

4. The device of claim 1 comprising means for releasably securing said die to the device, said securing means having means for quickly replacing said die.

5. The device of claim 4 wherein said heating means comprises a thermal heating element.

6. The device of claim 5 comprising means for enabling selection of a desired molding temperature; a thermocouple for measuring a temperature of said die; and a temperature controller, responsive to said temperature selecting means and said thermocouple, for controlling said heating means to regulate the die temperature at about the desired molding temperature.

7. The device of claim 6 comprising a dwell timer, and means for enabling adjustment of said dwell timer to select a desired dwell time and wherein said axial moving means pauses with the catheter in said die during the desired dwell time.

8. The device of claim 7 wherein said axial moving means comprises means for enabling selection of a desired axial moving distance, and wherein said step motor is responsive to said distance selecting means for axially moving the catheter into said die the desired axial moving distance.

9. A device for tipping catheters comprising:
   a die for molding a tip on a catheter;
   means for hating said die;
   means for holding an untipped catheter in an axially aligned position relative to said die;
   a step motor, coupled to said holding means, for axially advancing said holding means to move the held catheter into said die;
   a controller, responsive to said axial advancing rate selection enabling means, for actuating said step motor to axially advance the held catheter into said die; and
   means for enabling selection of a desired axial advancing rate without reprogramming said controller.

10. The device of claim 9 wherein said holding means comprises a pad, and means for clamping said pad against the catheter.

11. The device of claim 10 wherein said pad includes a groove to minimize pinching of the clamped catheter.

12. The device of claim 11 comprising a cool timer, and means connected to said die for providing a flow of air through the catheter, and wherein said controller is responsive to said cool timer for actuating said air providing means to supply a flow of air through the catheter; means for enabling adjustment of said cool timer to select a desired cool time without reprogramming said controller.

13. The device of claim 9 comprising means for releasably securing said die to the device, said securing means having means for quickly replacing said die.

14. The device of claim 13 comprising means for enabling selection of a desired axial advancing distance; and wherein said controller is responsive to said axial advancing distance selection enabling means for actuating said step motor to axially advance the held catheter into said die the desired distance.

15. The device of claim 14 comprising means for enabling selection of a desired molding temperature, a thermocouple for measuring a temperature of said die, and wherein said controller is responsive to said molding temperature selection enabling means and said thermocouple for controlling said heating means to regulate the die temperature to about the desired molding temperature.

16. The device of claim 15 comprising a dwell timer, and means for enabling adjustment of said dwell timer to select a desired dwell time, and wherein said controller is responsive to said dwell timer for pausing said step motor to retain the catheter within said die during the desired dwell time.

17. In a catheter tipping device of the type including a die, means for heating the die and means for moving an untipped catheter into the die, the improvement comprising:
means for removably securing said die to the device to enable relatively quick and easy replacement of said die;
a cool timer;
means connected to the die for providing a flow of air through the tipped catheter to cool it;
a controller;
means for enabling selection of a desired advancing rate without reprogramming said controller; and
means for enabling adjustment of said cool timer to select a desired cool time without reprogramming said controller;
said controller responsive to said advancing rate selection enabling means for actuating the moving means to advance the untipped catheter into said die at the desired rate, and responsive to said cool timer for actuating said air providing means to provide a flow of air through the catheter during the desired cool time.

18. The device of claim 17 wherein the moving means comprises a step motor.

* * * * *